US012691276B2

(12) United States Patent
Granegger et al.

(10) Patent No.: US 12,691,276 B2
(45) Date of Patent: Jul. 28, 2026

(54) BLOOD PUMP

(71) Applicant: CHARITÉ—UNIVERSITAETSMEDIZIN BERLIN, Berlin (DE)

(72) Inventors: Marcus Granegger, Perchtoldsdorf (AT); Tim Bierewirtz, Berlin (DE); Marcel Nicolai, Berlin (DE); Ulrich Kertzscher, Berlin (DE)

(73) Assignee: CHARITÉ—UNIVERSITAETSMEDIZIN BERLIN, Berlin (DE)

( * ) Notice: Subject to any disclaimer, the term of this patent is extended or adjusted under 35 U.S.C. 154(b) by 631 days.

(21) Appl. No.: 18/043,464

(22) PCT Filed: Sep. 2, 2021

(86) PCT No.: PCT/EP2021/074196
§ 371 (c)(1),
(2) Date: Feb. 28, 2023

(87) PCT Pub. No.: WO2022/294916
PCT Pub. Date: Mar. 10, 2022

(65) Prior Publication Data
US 2023/0310832 A1     Oct. 5, 2023

(30) Foreign Application Priority Data
Sep. 3, 2020     (EP) ..................................... 20194301

(51) Int. Cl.
*A61M 60/258*     (2021.01)
*A61M 60/122*     (2021.01)
(Continued)

(52) U.S. Cl.
CPC ........ *A61M 60/258* (2021.01); *A61M 60/226* (2021.01); *A61M 60/462* (2021.01); *A61M 60/122* (2021.01)

(58) Field of Classification Search
CPC .............. A61M 60/258; A61M 60/226; A61M 60/462; A61M 60/122
See application file for complete search history.

(56) References Cited

U.S. PATENT DOCUMENTS

| | | | |
|---|---|---|---|
| 4,213,207 A | 7/1980 | Wilson | |
| 4,375,941 A | 3/1983 | Child | |
| 2011/0144744 A1 | 6/2011 | Wampler | |

FOREIGN PATENT DOCUMENTS

| | | | | |
|---|---|---|---|---|
| WO | 2020/185630 | 9/2020 | | |
| WO | WO-2020185630 A1 * | 9/2020 | .......... | A61M 60/531 |

OTHER PUBLICATIONS

International Search Report mailed on Dec. 10, 2021 in PCT/EP2021/074196.

(Continued)

*Primary Examiner* — Lindsey G Wehrheim
(74) *Attorney, Agent, or Firm* — Fox Rothschild LLP

(57) ABSTRACT

The present disclosure refers to a blood pump as defined in claim 1 comprising: —a pump housing with a cylindrical piston chamber; —an axially and rotatably slidable free floating piston centrally positioned within the cylindrical piston chamber thereby dividing the cylindrical piston chamber into a left chamber and a right chamber, wherein the left chamber and right chamber each include an inlet and outlet transversely arranged to and communicating with the left chamber, respectively right chamber; —a linear motor unit configured to generate an electromagnetically driven translational motion of the piston along the longitudinal axis of the piston chamber alternately between a first end position and a second end position; and—at least one rotary motor unit configured to generate an electromagnetically driven rotary motion of the piston around the longitudinal axis (Continued)

during the translational motion of the piston between the first end position and the second end position.

13 Claims, 6 Drawing Sheets

(51) Int. Cl.
  *A61M 60/226*   (2021.01)
  *A61M 60/462*   (2021.01)

(56)       References Cited

OTHER PUBLICATIONS

Chinese Office Action issued on Apr. 24, 2025 in application No. CN 202180053653.4.

* cited by examiner

A - A

B - B

BLOOD PUMP

CROSS-REFERENCE TO RELATED APPLICATIONS

This application is a § 371 national phase entry of International Patent Application No. PCT/EP2021/074196, filed on Sep. 2, 2021, which claims priority to and the benefit of European Patent Application No. 20194301.6 filed on Sep. 3, 2020, both of which are hereby incorporated herein by reference in their entireties.

FIELD OF THE INVENTION

The present invention relates to a blood pump.

TECHNOLOGICAL BACKGROUND

With one third of all causes of death, cardiovascular diseases account for the most frequent cause of deaths worldwide. One of the most common cardiovascular diseases is heart failure, which affects at least 26 million people. In severe cases of heart failure where pharmacologic treatment is not effective, heart transplantation is the therapy of choice. However, donor organs are rare. Therefore, mechanical blood pumps like ventricular assist devices (VAD) or total artificial hearts (TAH) have been developed to bridge the time until a donor heart is available or to replace the heart completely. With the rise of small, implantable rotary blood pumps (RBPs) used as ventricular assist devices, the importance of larger pulsatile pumps in the treatment of end-staged heart failure declined. Available pulsatile systems are based on positive displacement pumps with valves, and require large pneumatic driving units, which limits the quality of life substantially.

In spite of the efficacy of RBPs, patients suffer from several adverse events related to the compromised hemocompatibility of these devices, leading to von Willebrand factor deficiency, platelet activation, hemolysis, and resulting in major bleedings, cerebral strokes, and pump thrombosis. Although the shear rate in contemporary clinical pulsatile devices is lower, the valve regions are susceptible to thrombosis due to the long residence times and disturbed flow patterns around the valve discs or leaflets.

Existing mechanical circulatory support (MCS) devices ensure survival and improve the quality of life of most recipients, however, current RBPs are associated with serious adverse events (thromboembolic and bleeding complications) caused by their poor hemocompatibility. Pulsatile devices have the potential to reduce trauma to the blood cells. However, the risk of thrombosis, caused by the interaction between blood and artificial materials comprising the device, remains.

Recent observations highlight the medical need for hemocompatible blood pumps used as ventricular assist devices and total artificial hearts: Critical complications taint the long-term performance of all implantable rotary blood pumps. Serious adverse events are stirred by the non-physiological flow patterns and the interaction between pump and the cardiovascular system. Only 20% of these patients are free from severe adverse events including right heart failure, bleeding or strokes after 24 months. Life quality is therefore strongly impaired and new developments are urgently needed. A small, implantable hemocompatible TAH with a low risk of complications constitutes the urgently needed treatment for adult patients with biventricular failure and children with congenital heart (e.g. Fontan patients).

It is thus an object of the present invention to overcome or reduce at least some of the drawbacks of the prior art and to develop a new pumping concept delivering pulsatile flow to the cardiovascular system.

SUMMARY OF INVENTION

Embodiments of the present disclosure seek to solve at least one of the problems existing in the prior art to at least some extent. In particular, the present disclosure refers to a blood pump as defined in claim 1 comprising:
- a pump housing with a cylindrical piston chamber;
- an axially and rotatably slidable free floating piston centrally positioned within the cylindrical piston chamber thereby dividing the cylindrical piston chamber into a left chamber and a right chamber, wherein the left chamber and right chamber each include an inlet and outlet transversely arranged to and communicating with the left chamber, respectively right chamber;
- a linear motor unit configured to generate an electromagnetically driven translational motion of the piston along the longitudinal axis of the piston chamber alternately between a first end position and a second end position; and
- at least one rotary motor unit configured to generate an electromagnetically driven rotary motion of the piston around the longitudinal axis during the translational motion of the piston between the first end position and the second end position.

Further aspects of the present disclosure could be learned from the dependent claims or the following description.

BRIEF DESCRIPTION OF THE DRAWINGS

Features will become apparent to those of ordinary skill in the art by describing in detail exemplary embodiments with reference to the attached drawings in which.

DETAILED DESCRIPTION OF THE INVENTION

Figure 1A:
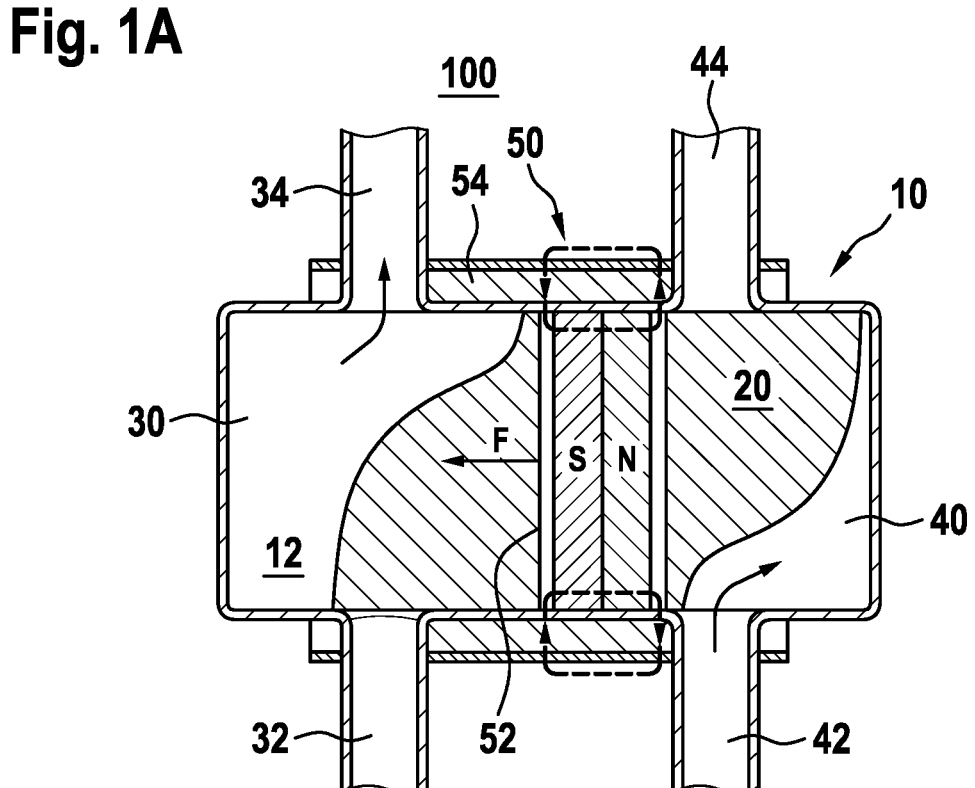
FIGS. 1A/1B illustrate cross sectional views on an exemplary embodiment of the blood pump.

Features of the inventive concept and methods of accomplishing the same may be understood more readily by reference to the following detailed description of an embodiment and the accompanying drawings. The present invention, however, may be embodied in various different forms, and should not be construed as being limited to only the illustrated embodiments herein. Rather, this embodiment is provided as example so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof will not be repeated. In the drawings, the relative sizes of elements, layers, and regions may be exaggerated for clarity.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

General Concept

The present disclosure generally refers to a blood pump comprising:

- a pump housing with a cylindrical piston chamber;
- an axially and rotatably slidable free floating piston centrally positioned within the cylindrical piston chamber thereby dividing the cylindrical piston chamber into a left chamber and a right chamber, wherein the left chamber and right chamber each include an inlet and outlet transversely arranged to and communicating with the left chamber, respectively right chamber;
- a linear motor unit configured to generate an electromagnetically driven translational motion of the piston along the longitudinal axis of the piston chamber alternately between a first end position and a second end position; and
- at least one rotary motor unit configured to generate an electromagnetically driven rotary motion of the piston around the longitudinal axis during the translational motion of the piston between the first end position and the second end position.

The new pumping concept delivers pulsatile flow to the cardiovascular system with a single moving part, without risk prone valves and the potential for an outstanding hemocompatibility. The size of the design theoretically facilitates implantation in pediatric and adult patients.

According to the present disclosure, the blood pump includes a first motor unit which is configured to generate an electromagnetically driven translational motion of the movable piston and at least one another second motor unit configured to generate an electromagnetically driven rotary motion of the movable piston around the longitudinal axis of the cylindrical piston chamber. The linear and rotational motions must be performed together only in so far as they lead to the two mentioned end positions of the piston. In other words, during the translational motion or movement of the piston from one end position towards the other end position, the rotational motion or movement can be uniform or over time at different speeds. Preferably, the rotary motion may be a continuously rotary motion. The same applies with respect to the translational motion.

Through the superposition of the two movement sequences the present blood pump combines the advantages of both pulsatile and rotary blood pumps of the state of art. In particular, the size of the blood pump may be comparable to other TAHs under development based on rotary principles. The single moving part, i.e. the piston, enhances reliability of a pulsatile valveless pump to levels of rotary blood pumps. The blood pump may prove superior to common pulsatile devices in terms of reliability and risk of thrombosis due to the valveless design. At the same time, the pulsatile pumping principle with much lower velocities and shear rates than in RBPs may demote adverse events related to the working principle of modern RBPs. The size of the pump for the adult population may be approx. 10×5 cm, which is much smaller than comparable systems. Additionally, the design can be downscaled for the use in pediatric patients.

According to one embodiment, the linear motor unit is construed as a multi-phase (for example 2- or 3-phase) linear induction motor (LIM) including an axially polarized ring-shaped permanent magnet array positioned within the piston and segmented windings wired around the cylindrical piston chamber. Generally, a linear electric motor's primary typically consists of a flat magnetic core with transverse slots that are often straight cut with coils laid into the slots, with each phase giving an alternating polarity so that the different phases physically overlap. The secondary is frequently a sheet of aluminium, often with an iron backing plate. Some LIMs are double sided with one primary on each side of the secondary, and, in this case, no iron backing is needed. However, according to the present embodiment, a regulated electromagnet serves as stator (i.e. represents the primary) whereas the secondary includes a permanent magnet positioned in the moveable piston. Thus, the electric motor is a brushless motor and any wear as well as spark formation could be avoided.

In addition to the use of the before mentioned multi-phase linear induction motor or separately thereof, the rotary motor unit may be construed as a multi-phase (for example 2- or 3-phase) rotational induction motor including a radially polarized permanent magnet array positioned within the piston and segmented windings wrapped along an axial side and circumference the cylindrical piston chamber. The segmented winding may include soft magnetic back yokes and multi (for example 2 or 3) phases of wired coils wrapped along an axial side and circumference the cylindrical piston chamber. The radially polarized permanent magnet array may be positioned closed to each base surfaces of the piston facing the left chamber and the right chamber. Thus, the stator of rotary motor unit is represented by the wrapped coil arrangement and the part in motion includes a permanent magnet. Once again, such an arrangement allows a brushless implementation of the rotary motor unit.

According to another embodiment, the inlet and outlet of the left chamber are positioned on opposite sides of the cylindrical piston chamber, respectively the inlet and outlet of the right chamber are positioned on opposite sides of the cylindrical piston chamber.

Further, a piston length may be in the range of 60 to 100 mm and a piston radius may be in the range of 40 to 60 mm. Separately or in addition thereof, a volume of the left or right chamber may be in the range of 5 to 50 ml. If the before-mentioned dimensions are maintained, the blood pump may be used as a full implant.

Another embodiment provides that a motion frequency of the translational motion of the piston is in the range of 2 to 10 Hz. This ensures the generation of sufficient hydrodynamic forces to bear the piston within the cylindric housing.

The piston may be further construed such that in the first end position a lateral surface of the piston closes the inlet of the left chamber and the outlet of the right chamber, whereas the outlet of the left chamber and the inlet of the right chamber are open, and whereby the closing situation of the inlets and outlets is exactly reversed in the second end position. In other words, inlets and outlets of each chamber are alternately closed and opened, i.e. if the inlet of a certain chamber is open its outlet will be closed. In addition, if an inlet of one of the chambers is open, the inlet of the other chamber is closed.

In particular, the piston has a left base surface facing the left chamber and a right base surface facing the right chamber. According to an embodiment, a curved part of the left base surface is inwardly curved such that (i) in the first end position of the piston the outlet of the left chamber is open while the inlet of the left chamber is closed and (ii) in the second end position of the piston the inlet of the left chamber is open while the outlet of the left chamber is closed. In addition, a part of the right base surface is inwardly curved such that (i) in the first end position of the piston the inlet of the right chamber is open while the outlet of the right chamber is closed and (ii) in the second end position of the piston the outlet of the right chamber is open while the inlet of the right chamber is closed. In other words, the base surfaces on the left and right side of the piston do not extend perpendicular to the longitudinal axis of the piston. Said base surfaces are also not planar, but have a surface contour, which includes an inwardly (i.e. towards the piston) curved area. This allows pressure peaks to be avoided during pumping.

The surface contour of the left base surface and the surface contour of the right base surface may be point symmetrical to each other. In this way, the manufacturing process can be simplified.

According to another embodiment, a shunt is connected between at least one of the left and right chambers or the inlets of the left and right chambers. The shunt is configured to allow pressure balancing between both chambers. For example, the shunt may be realised by a groove within the pump housing extending between the two chambers, respectively ending into the left and the right inlet.

In alternative or additional the rotary motion of the piston around the longitudinal axis during the translational motion of the piston chamber between the first end position and the second end position is a non-synchronous or a non-uniform rotary motion. In other words, at least one of these two motions indicate a discontinuous behaviour. Thereby, an accurate balancing of the output of the left and right chamber is possible. In other words, by adapting the rotating speed the pump efficiency of each chamber can be adapted, thereby adapting the amount of discharged blood. This measure may for example prevent pulmonary congestion or so-called suction events.

According to another embodiment of the present disclosure, a hydrodynamic bearing may be provided between the outer surface of the piston and the inner surface of the piston chamber of the pump housing. This bearing ensures a smooth piston motion without the risk for dry friction and material wear. Specifically, the hydrodynamic bearing may have a gap clearance of less than 100 µm. In that case only a small amount of blood components may enter such small hydrodynamic bearings, consequently leading to low blood trauma in these regions.

Exemplary Embodiments

Figure 1B:
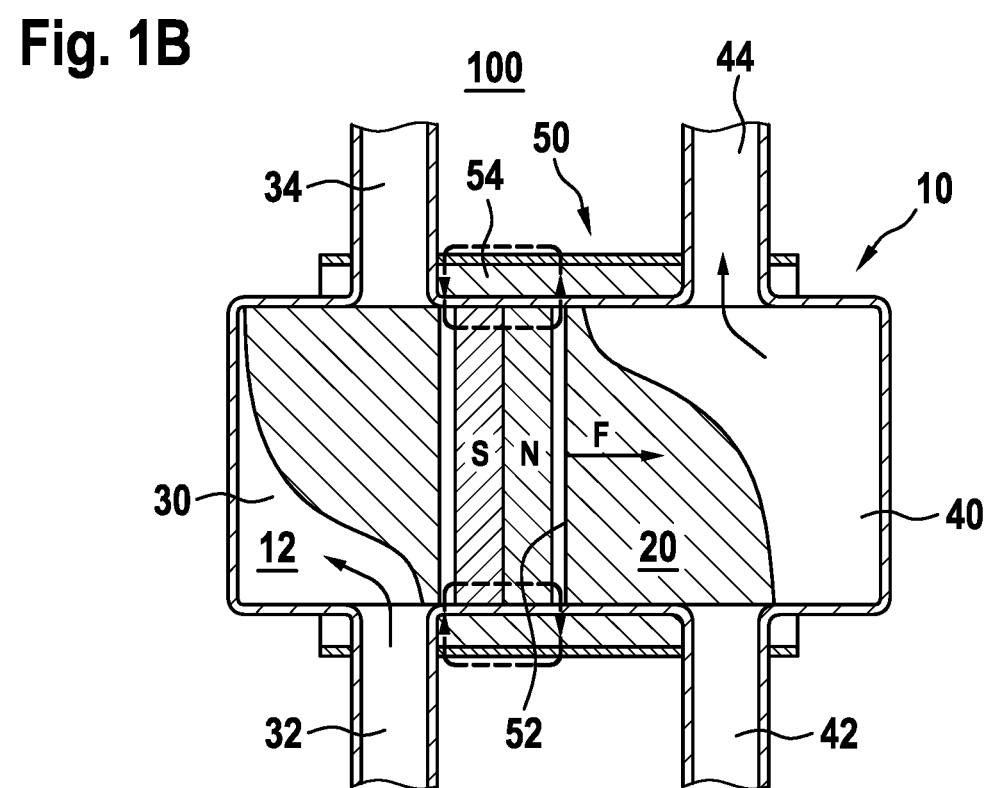

FIGS. 1A and 1B illustrate cross sectional views on an exemplary embodiment of the blood pump 100. The blood pump 100 includes a pump housing 10 with a cylindrical piston chamber 12. An axially and rotatably slidable free floating piston 20 centrally positioned within the cylindrical piston chamber 12 thereby dividing the cylindrical piston chamber 12 into a left chamber 30 and a right chamber 40. The left chamber 30 and right chamber 40 each include an inlet 32, 42 and outlet 34, 44 transversely arranged to and communicating with the left chamber 30, respectively right chamber 40.

A linear motor unit 50 is configured to generate an electromagnetically driven translational (or translatory) motion of the piston 20 along the longitudinal axis of the piston chamber 12 alternately between a first end position shown in FIG. 1A and a second end position shown in FIG. 1B. Here, the linear motor unit 50 is construed as a 3-phase linear induction motor including an axially polarized ring-shaped permanent magnet array 52 positioned within the piston 20 and segmented windings 54 wired around the cylindrical piston chamber 12.

A rotary motor unit is configured to generate an electro-magnetically driven partially rotary motion of the piston 20 around the longitudinal axis during the translational motion within the piston 20 between the first end position and the second end position. For sake of clarity, FIGS. 1A and 1B do not illustrate details thereof, but the rotary motor unit will be described in detail below. For the understanding of the pumping mechanism in FIGS. 1A and 1B it is only important that the rotary motor unit allows to make the piston a 180° turn during movement from the first end position into the second end position, respectively a 180° turn back from the second end position into the first end position.

The two inlets 32, 42 of the pump 100 are connected to the left and right atria, respectively. The outlets 34, 44 are anastomosed to the pulmonary artery and the aorta. The piston 20 is electromagnetically driven in a shuttling translationally and in a uniform rotatory motion inside a cylindrical piston chamber 20. Thereby the piston 20 divides the pump housing 10 into left and right chambers 30, 40, with one inlet 32, 42 and outlet 34, 44 each. The translational motion from the first end position illustrated in FIG. 1A towards the second end position illustrated in FIG. 1B causes a filling of one chamber, here the right chamber 40 while the other chamber—here the left chamber 30—is emptied simultaneously. Through the rotation, the opening of the inlet 32, 42 and outlet 34, 44 of both chambers 30, 40 are controlled, so mechanical check valves are obsolete. With this combination of rotation and translation, the entire pump function of both the right and the left heart is accomplished by only one moving part.

In FIGS. 1A and 1B the pumping and actuation principle is depicted by arrows. The filling of the right chamber 40 is accompanied with simultaneously discharging of the left chamber 30. The translational movement is achieved by energizing wired coil of the windings 54 causing a Lorentz force $F_L$ on the piston 20. The translational movement is superimposed by a rotational 180° movement of the piston 20. The inlet 42 of the right chamber 40 and the outlet 34 of the left chamber 30 is closed in the second end position of the piston 20 without the need of valves. When the current in the wired coils is inverted, the piston 20 is forced backwards to the first end position discharging the right chamber 40 while filing the left chamber 30. The dashed lines indicate the magnetic flux path of the permanent magnet array 52.

The motion frequency of the piston 20 may be in the range of 3 to 5 Hz to support a patient at rest, causing relatively low velocities compared to state-of-the-art rotary blood pumps and potentially resulting in significantly lower blood trauma. A superior washout potential is expected because of marginal stagnation areas within the pump 100 and a low priming volume. The simple geometry permits the use of ultrahigh precision leading to smooth surfaces in blood contact, mitigating the risk for thrombus formation.

The outer surface of the piston 20 and the inner surface of the piston chamber 12 of the pump housing 10 may be manufactured with ultrahigh precision because of their simple rotational symmetry. A hydrodynamic bearing may be provided between the outer surface of the piston 20 and the inner surface of the piston chamber 12 of the pump housing 10 (not shown). The hydrodynamic bearing may have a gap clearance of less than 100 μm. This bearing ensures a smooth piston motion without the risk for dry friction and material wear. Recent findings suggest that only a small amount of blood components may enter such small hydrodynamic bearings, consequently leading to low blood trauma in these regions.

The electromagnetic motor composed of the linear motor unit 50 and at least one rotary motor unit actuates the piston 20 in an efficient way compared to other pulsatile blood pumps: For the translational motion, two wired coils around the middle part of the pump 100 housing are energized in opposite current directions for an optimal force generation. The rotary motion will be achieved by one or two radial flux motors.

Figure 2A:
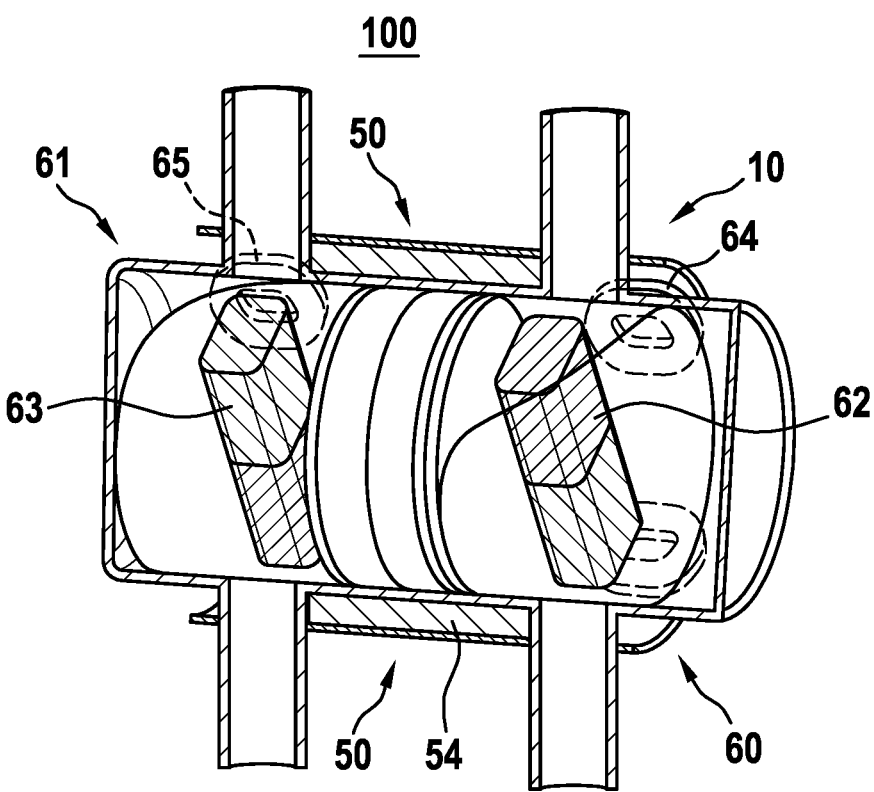
FIGS. 2A/2B illustrate an electromagnetic driving system of the blood pump according to the exemplary embodiment.
Figure 2B:
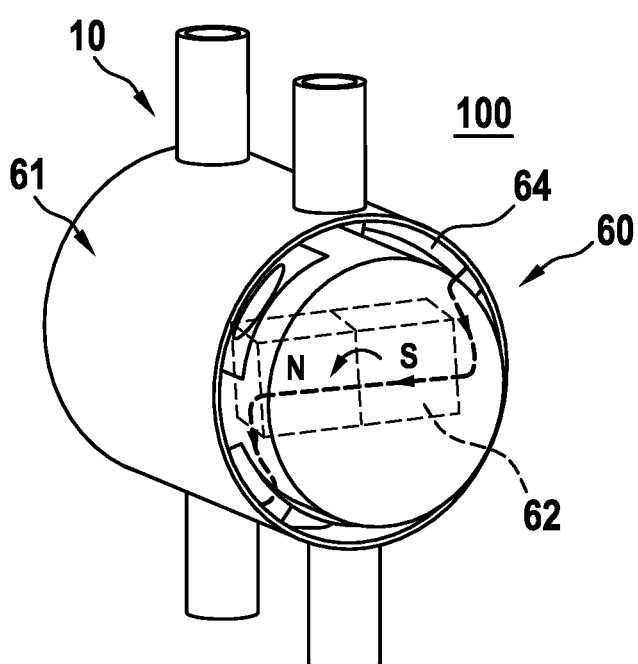

In FIGS. 2A/2B the actuation system is depicted in more detail. Besides the centrally positioned linear motor unit 50 two rotary motor units 60, 61 are arranged left and right thereof. Each rotary motor unit 60, 61 unit is construed as a multi-phase rotational induction motor including a radially polarized permanent magnet array 62, 63 positioned within the piston 20 and segmented windings 64, 65 including soft magnetic back yokes and multi phases of wired coils wrapped along an axial side and circumference the cylindrical piston chamber 12. Here, the rotary motor units 60, 61 are realized as 2-phase unipolar permanent magnet type stepper motors. A magnetic flux path of the rotary motor unit 60 is illustrated by the dashed line in FIG. 2B resulting in a torque moment that causes the rotation of the piston 20.

Figure 3A:
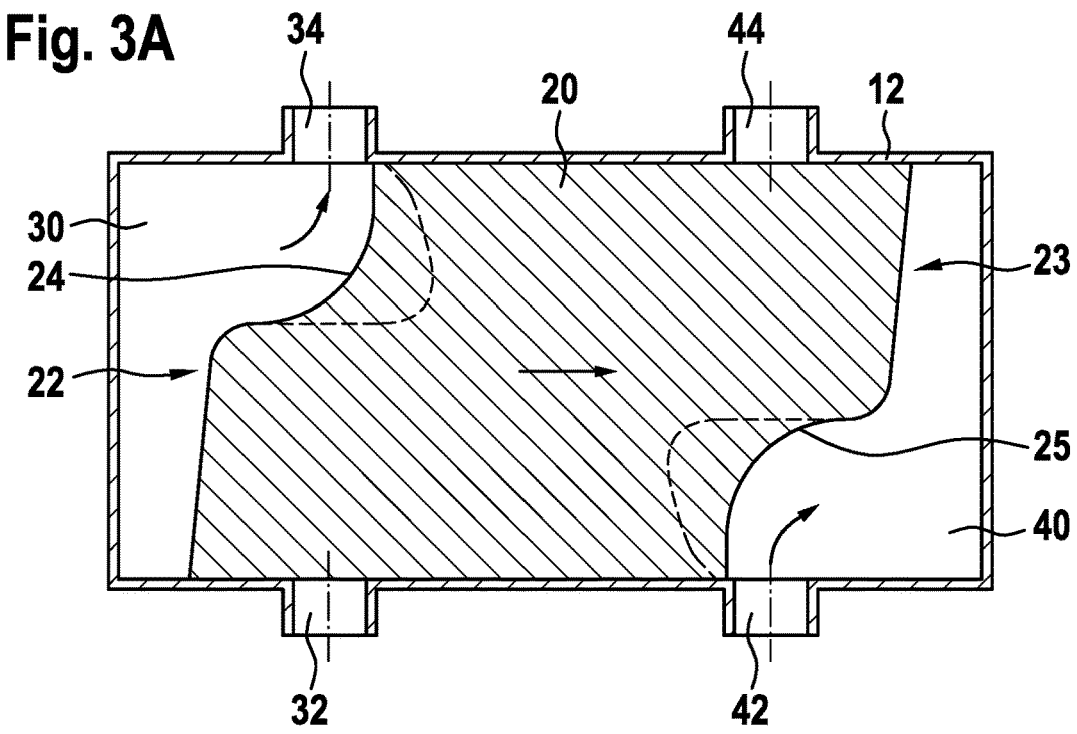
FIGS. 3A/3B illustrate cross sectional views of the piston chamber and piston according to the exemplary embodiment.
Figure 3B:
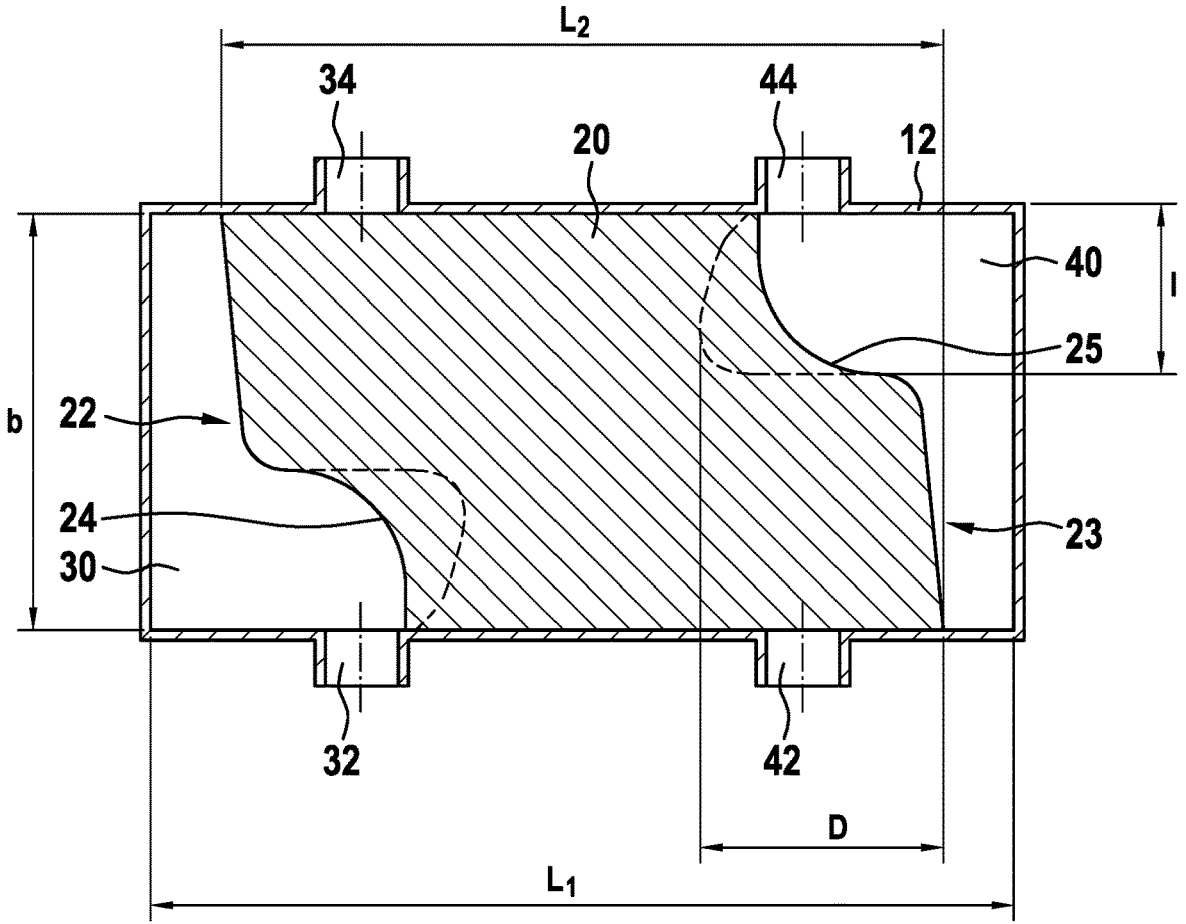

FIGS. 3A and 3B are cross sectional views of the piston chamber 12 and the piston 20 according to the exemplary embodiment. The two inlets 32, 42 may have a diameter in the range of 5 to 25 mm and are connected to the left and right atria for example via conically shaped textile materials, respectively. The outlets 34, 44 may have a similar diameter of 5 to 25 mm and may be connected to graft materials and anastomosed to the pulmonary artery and the aorta. As already mentioned above, the piston 20 is electromagnetically driven in a shuttling translationally and in a uniform rotatory motion inside the cylindrical piston chamber 12. As illustrated in FIG. 3A, the translational motion from the left chamber 30 in direction to the right chamber 40 pumps blood and fills through the outlet 34 into the aorta. Simultaneously, the right chamber 40 is filled through the inlet 42. The left inlet 32 and the right outlet 44 are closed by the piston 20. As shown in FIG. 3B, the rotation of the piston 20 opens the inlet 32 of the left chamber 30 and closes the inlet 42 of the right chamber 40. The translational movement from the right to the left discharges the right chamber 40 and fills the left chamber 30. Only exemplary: for an adult population pump a total length $L_1$ may be 100 mm, a length $L_2$ of the piston 20 may be 83 mm, and a diameter D of the piston chamber 12 may be 50 mm.

Furthermore, the piston 20 has a left base surface 22 facing the left chamber 30 and a right base surface 23 facing the right chamber 40. A curved part 24 (or notch) of the left base surface 22 is inwardly curved such that (i) in the end position of the piston 20 illustrated in FIG. 3A the inlet 32 of the left chamber 30 is open while the outlet 34 of the left chamber 30 is closed and (ii) in the end position of the piston 20 illustrated in FIG. 3B the inlet 32 of the left chamber 30 is open while the outlet 34 of the left chamber 30 is closed. In addition, a curved part 25 (or notch) of the right base surface 23 is inwardly curved such that (i) in the first end position of the piston 20 the inlet 42 of the right chamber 40 is open while the outlet 44 of the right chamber 40 is closed and (ii) in the second end position of the piston 20 the outlet 44 of the right chamber 40 is open while the inlet 42 of the right chamber 40 is closed. In other words, the base surfaces 22, 23 on the left and right side of the piston 20 do not extend perpendicular to the longitudinal axis of the piston 20. Said base surfaces 22, 23 are also not planar, but have a surface contour, which includes an inwardly (i.e. towards the piston 20) curved area. This allows pressure peaks to be avoided during pumping, so that the hemocompatibility is improved.

According to the exemplary embodiment, the motion frequency of the piston 20 may be in the range of 2 to 10 Hz. The course of resulting flow and pressure in the left chamber 30 is shown in in FIG. 4. The simple geometry of the blood piston 20 and piston chamber 12 permits the use of ultrahigh precision leading to smooth surfaces in blood contact, mitigating the risk for thrombus formation. Each stroke pumps and fills the chambers 30, 40 with a volume of 5 to 50 ml.

Only exemplary, the height H of the curved parts 24, 25 may be 20 mm and the depth D of the curved parts 24, 25 may be 28 mm. As could be further seen from FIGS. 3A and 3B, the surface contour of the left base surface 22 and the surface contour of the right base surface 23 are point symmetrical to each other. In this way, the manufacturing process can be simplified and the pump volumes of the two chambers 30, 40 are essentially equal. This way, also optimal operation with a minimum risk for blood trauma may be ensured.

Figures 4, 5:
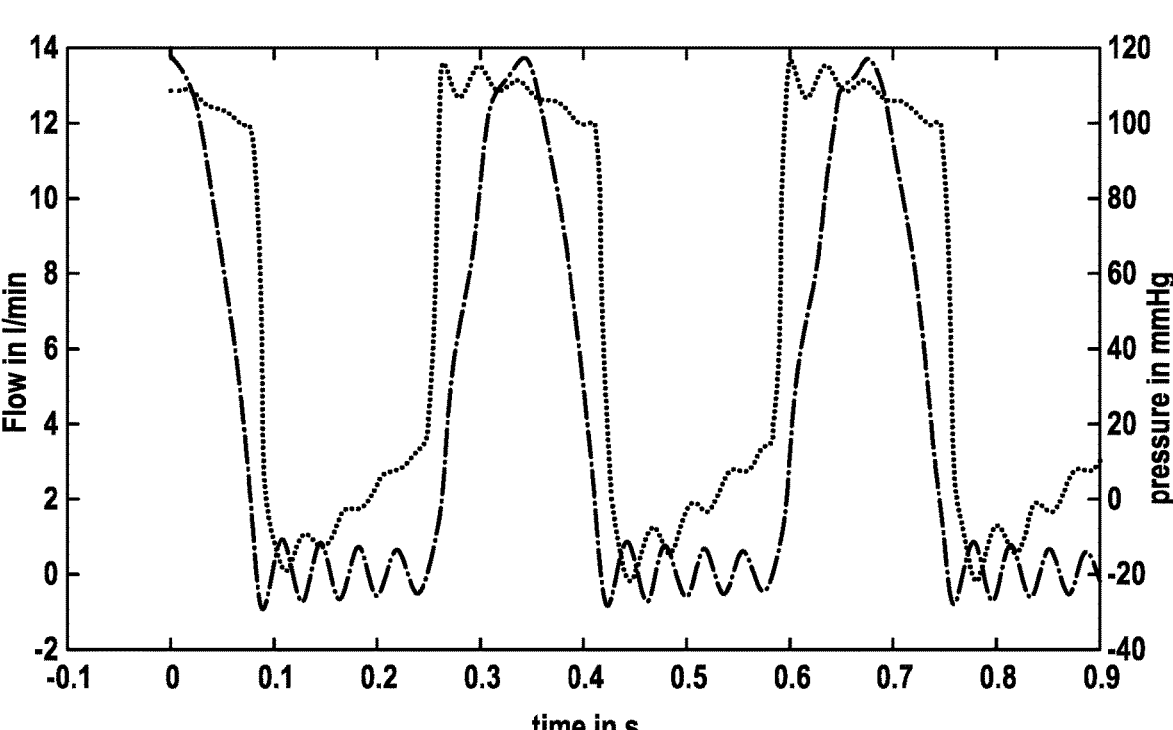
FIG. 4 show the course of the outlet flow and pressure in one of the chambers over the time.
FIG. 5 show the theoretical load capacity of the blood pump in dependency of the eccentricity.
Figure 6A:
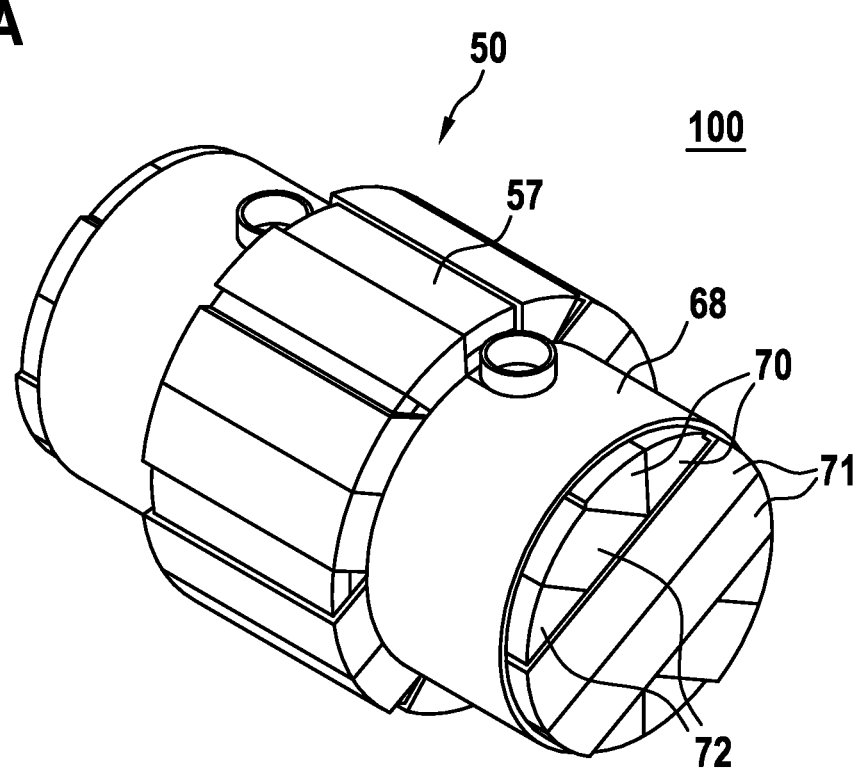
FIGS. 6A-6D illustrate another exemplary embodiment of the blood pump.
Figure 6B:
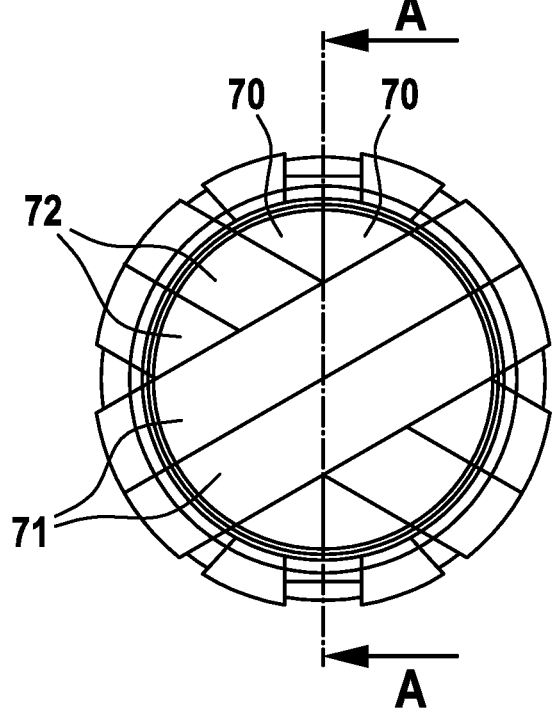
Figures 6C, 6D:
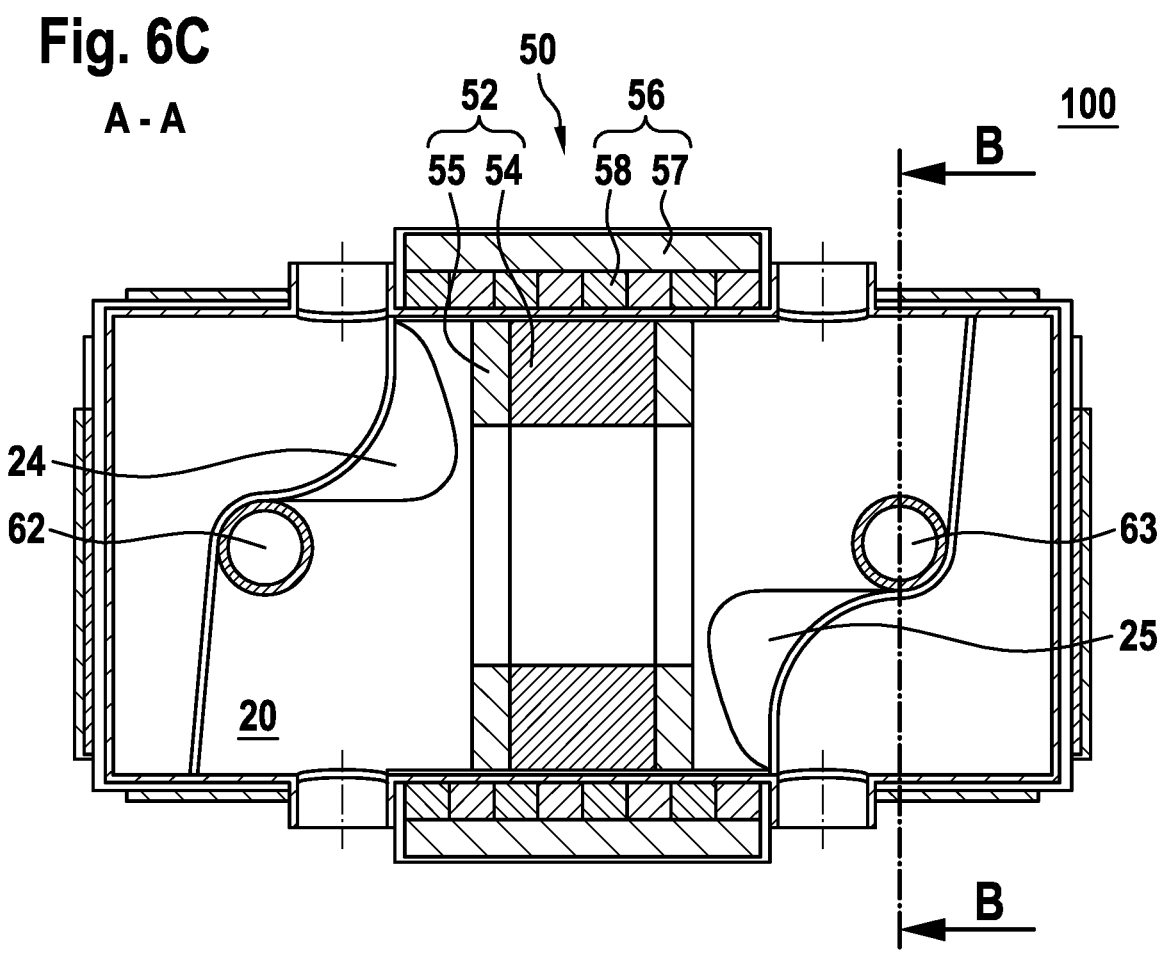

The outer surface of the piston 20 (or piston shell area) and the inner surface of the piston chamber 12 (or inner shell area) of the pump housing can be manufactured with ultrahigh precision because of their simple rotational symmetry. Therefore, a hydrodynamic bearing with a gap clearance in the range of 0 to 500 μm can be realized. This bearing bears forces of >20 N and ensures a smooth piston motion at a maximum eccentricity of <95% without the risk for dry friction and material wear. An example for the load capacity of such a bearing at a gap of 75 μm is presented in FIG. 5 showing the theoretical load capacity of the blood pump in dependency of the eccentricity at a rotating frequency of 3 Hz.

The shuttling motion combined with the pressure differences between the left and right chamber 30, 40 may lead to an additional bearing stabilization due to the Lomakin effect. A certain gap clearance is required to permit enough gap flow which is necessary to cool the bearing region (heat due to motor coils) and to comply with the requirement of a maximal local temperature increase of 2° K. Additionally, due to the small gap only a small amount of blood components may enter such hydrodynamic bearing gaps, consequently leading to low blood trauma in these regions.

FIGS. 6A through 6D illustrate another exemplary embodiment of the blood pump 100. The electromagnetic motor system actuates the simultaneous translational and rotary piston motion. In the embodiment illustrated in the drawings, the translational motion is achieved by a linear motor unit 50. The linear motor unit 50 includes an axially polarized ring-shaped permanent magnet array 52 creating a magnetic field and composed of a permanent magnet 54 and soft magnetic material rings 55. The permanent magnet array 52 is positioned within the piston 20. Further, segmented windings 56 wired around the cylindrical piston chamber 12 and including a back yoke 57 and segmented copper coils 58. During operation, the soft magnetic material rings 55 lead the magnetic flux through the segmented copper coils 58 wired around the middle part of the piston chamber 12. A position dependent energization of the coil segments 58 creates a Lorentz force in axial direction.

For the rotary motion, permanent magnets 67 closed to the curved parts 24, 25 of the piston 20 are radially polarized and connected via a soft magnetic material hollow shaft 66 to form a light-weight permanent magnet arrays 62, 63. Soft magnetic back yokes 68 close the magnetic flux paths of the permanent magnets 67 and lead them through wired coils 70, 71, 72. 3 phases of wired coils 70, 71, 72 are wrapped along the axial side and circumference the whole piston chamber 12. In this way, a 3-phase slot-less permanent motor is realized.

REFERENCE SIGNS 10 pump housing
12 piston chamber
20 piston
22 left base surface
23 right base surface
24 curved part of the left base surface 22
25 curved part of the right base surface 23
30 left chamber
32 inlet of the left chamber 30
34 outlet of the left chamber 30
40 right chamber
42 inlet of the right chamber 40
44 outlet of the right chamber 40
50 linear motor unit
52 permanent magnet array
54 segmented windings
60, 61 rotary motor units
62, 63 permanent magnet arrays
64, 65 segmented windings
66 soft magnetic material hollow shaft
67 permanent magnet
68 Soft magnetic back yokes
70, 71, 72 wired coils
100 blood pump

The invention claimed is:

1. A blood pump (100) comprising:
a pump housing (10) with a cylindrical piston chamber (12);
an axially and rotatably slidable free floating piston (20) centrally positioned within the cylindrical piston chamber (12) thereby dividing the cylindrical piston chamber (12) into a left chamber (30) and a right chamber (40), wherein the left chamber (30) and right chamber (40) each include an inlet (32, 42) and outlet (42, 44) transversely arranged to and communicating with the left chamber (30), respectively right chamber (40);
a linear motor unit (50) configured to generate an electromagnetically driven translational motion of the piston (20) along the longitudinal axis of the piston chamber (12) alternately between a first end position and a second end position; and
at least one a rotary motor unit (60, 61) configured to generate an electromagnetically driven continuous rotary motion of the piston (20) around the longitudinal axis during the translational motion of the piston (20) between the first end position and the second end position;
wherein the rotary motor unit (60, 61) is construed as a multi-phase rotational induction motor including a radially polarized permanent magnet array (62, 63) positioned within the piston (20) and segmented windings (64, 65) wrapped along an axial side and circumference of the cylindrical piston chamber (12).

2. The blood pump of claim 1, wherein the linear motor unit (50) is construed as a multi-phase linear induction motor including an axially polarized ring-shaped permanent magnet array (52) positioned within the piston (20) and segmented windings (56) wired around the cylindrical piston chamber (12).

3. The blood pump of claim 1, wherein the radially polarized permanent magnet array (62, 63) is positioned closed to each base surface (22, 23) of the piston (20) facing the left chamber (30) and the right chamber (40).

4. The blood pump of claim 1, wherein the inlet (32) and outlet (34) of the left chamber (30) are positioned on opposite sides of the cylindrical piston chamber (12), respectively the inlet (42) and outlet (44) of the right chamber (40) are positioned on opposite sides of the cylindrical piston chamber (12).

5. The blood pump of claim 1, wherein a piston length is in the range of 60 to 100 mm and a piston radius is in the range of 40 to 60 mm.

6. The blood pump of claim 1, wherein a volume of the left or right chamber (30, 40) is in the range of 5 to 50 ml.

7. The blood pump of claim 1, wherein a motion frequency of the translational motion of the piston (20) is in the range of 2 to 10 Hz.

8. The blood pump of claim 1, wherein the piston (20) is construed such that in the first end position a lateral surface of the piston (20) closes the inlet (32) of the left chamber (30) and the outlet (44) of the right chamber (40), whereas the outlet (34) of the left chamber (30) and the inlet (42) of the right chamber (40) are open, and whereby the closing situation of the inlets (32, 42) and outlets (34, 44) is exactly reversed in the second end position.

9. The blood pump of claim 8, wherein the piston (20) has a left base surface (22) facing the left chamber (30) and a right base surface (23) facing the right chamber (40);
a curved part (24) of the left base surface (22) is inwardly curved such that (i) in the first end position of the piston (20) the outlet (34) of the left chamber (30) is open while the inlet (32) of the left chamber (30) is closed and (ii) in the second end position of the piston (20) the inlet (32) of the left chamber (30) is open while the outlet (34) of the left chamber (30) is closed; and
a curved part (25) of the right base surface (23) is inwardly curved such that (i) in the first end position of the piston (20) the inlet (42) of the right chamber (40) is open while the outlet (44) of the right chamber (40) is closed and (ii) in the second end position of the piston (20) the outlet (44) of the right chamber (40) is open while the inlet (42) of the right chamber (40) is closed.

10. The blood pump of claim 9, wherein the surface contour of the left base surface (22) and the surface contour of the right base surface (23) are point symmetrical to each other.

11. The blood pump of claim 1, wherein a shunt is connected between at least one of the left and right chambers (30, 40) or the inlets (32, 42) of the left and right chambers (30, 40), the shunt being configured to allow pressure balancing between both chambers (30, 40).

12. The blood pump of claim 1, wherein the partially rotary motion of the piston (20) around the longitudinal axis during the translational motion of the piston (20) between the first end position and the second end position is a non-synchronous or a non-uniform rotary motion.

13. The blood pump of claim 1, wherein a hydrodynamic bearing is provided between the outer surface of the piston (20) and the inner surface of the piston chamber (12) of the pump housing (10).

\* \* \* \* \*